United States Patent [19]

Meek

[11] Patent Number: 5,596,779
[45] Date of Patent: Jan. 28, 1997

[54] MEDICAL APPARATUS COMPRISING A MOVABLE PATENT TABLE HAVING A COMMON CONTROL MEMBER FOR OPERATING LONGITUDINAL DRIVE AND LOCKING MECHANISMS

[75] Inventor: Gerrit J. Meek, Eindhoven, Netherlands

[73] Assignee: U.S. Philips Corporation, New York, N.Y.

[21] Appl. No.: 328,309

[22] Filed: Oct. 24, 1994

[30] Foreign Application Priority Data

Oct. 27, 1993 [BE] Belgium .................. 09301146

[51] Int. Cl.$^6$ .................. A47B 13/00; H01H 9/00
[52] U.S. Cl. .................. 5/600; 5/601; 700/4
[58] Field of Search .................. 5/600, 601, 610, 5/611; 700/520, 337, 553, 4, 5 R, 6 R, 16 R

[56] References Cited

U.S. PATENT DOCUMENTS

| | | | |
|---|---|---|---|
| 3,612,509 | 10/1971 | Boston | 5/600 |
| 3,772,484 | 11/1973 | Roeser | 200/4 |
| 3,822,875 | 7/1974 | Schmedemann | |
| 4,761,000 | 8/1988 | Fischer | 5/600 |
| 4,926,456 | 5/1990 | Bock | 378/209 |

FOREIGN PATENT DOCUMENTS

| | | |
|---|---|---|
| 0506172 | 9/1992 | European Pat. Off. |
| 618238 | 6/1926 | France .................. 200/4 |
| 3226374 | 1/1984 | Germany .................. 5/600 |
| 1153750 | 9/1966 | United Kingdom |

*Primary Examiner*—Flemming Saether
*Attorney, Agent, or Firm*—Jack D. Slobod

[57] ABSTRACT

Medical apparatus includes a patient table (7) with a table support (9) and a table top (11) which is movable at least in its longitudinal direction relative to the table support, there being provided a first drive mechanism (21) to assist said movement, if desired; the table top can be locked relative to the table support by means of a locking mechanism (23). The apparatus comprises a common control member (43) for moving the table top (11) in the longitudinal direction and for operating the first drive mechanism (21) and the locking mechanism (23). The control member comprises a link rod (57) which is movable in its longitudinal direction and which cooperates with a switch (67) for operating the locking mechanism, and also comprises a control element (71) which is movable transversely of the longitudinal direction of the link rod and which cooperates with a sensor (73) which supplies an output signal for control of the drive mechanism. The link rod (57) and the control element (71) are movable by means of a common control knob (59) whereby the table top (11) can be moved also without assistance from the first drive mechanism (21). Consequently, control of the movements of the table top (11) is very simple and orderly.

19 Claims, 2 Drawing Sheets

MEDICAL APPARATUS COMPRISING A MOVABLE PATENT TABLE HAVING A COMMON CONTROL MEMBER FOR OPERATING LONGITUDINAL DRIVE AND LOCKING MECHANISMS

BACKGROUND OF THE INVENTION

1. Field of the Invention

The invention relates to a medical apparatus, including a patient table with a table support and a table top which is movable at least in its longitudinal direction relative to the table support, there being provided a first drive mechanism for assisting this movement, if desired, it being possible to lock said table top relative to the table support by means of a locking mechanism.

2. Description of the Prior Art

An apparatus of this kind is known from EP-A-0 506 172. The known apparatus is provided with a motor for moving the table top in the longitudinal direction, the table top being displaced on rollers which can be blocked by way of the locking device. Separate control members are provided for control of the motor and the locking device. The control members are accommodated on a console which also comprises a large number of other control members for other functions of the apparatus. Because of this large number of control members, the console is rather cluttered and operation requires close attention.

SUMMARY OF THE INVENTION

It is an object of the invention to improve an apparatus of the kind set forth so that control is simplified. To achieve this, the apparatus in accordance with the invention is characterized in that it comprises a common control member for moving the table top in the longitudinal direction and for controlling the first drive mechanism and the locking mechanism, which control member comprises a link rod which is movable in its longitudinal direction and which cooperates with a switch in order to operate the control mechanism, and also comprises a control element which is movable transversely of the longitudinal direction of the link rod and which cooperates with a sensor which supplies an output signal for operating the drive mechanism, the link rod and the control element being movable by means of a common control knob whereby the table top can be moved also without assistance from the first drive mechanism. Thanks to these improvements, full control of the table top can be exercised with one hand, so that the person operating the apparatus can pay more attention to other functions of the apparatus.

An embodiment of the apparatus in accordance with the invention which can be realized in a technically simple manner is characterized in that the link rod is journalled so as to be movable in its longitudinal direction in a bearing sleeve which supports the control element and which can be tilted about a shaft extending transversely of its longitudinal direction, the control knob being attached to a first end of the link rod which is situated near a first end of the bearing sleeve, the arrangement being such that by pressing the control knob the link rod can be moved in its longitudinal direction from a first position to a second position, the bearing sleeve itself being tiltable about said shaft from a neutral position into two opposite directions under the influence of a lateral force exerted on the control knob, the force exerted on the control knob being transferred to the bearing sleeve via the link rod. In order to ensure that the control member always reaches a predetermined position automatically when the control knob is released, a preferred embodiment of the apparatus in accordance with the invention is characterized in that there are provided first resilient means which exert a force on the link rod which drives the link rod to its first position, there also being provided second resilient means which exert a force on the bearing sleeve which drives the bearing sleeve to its neutral position.

There are various possibilities to connect the control element to the bearing sleeve. A very simple solution is characterized in that the control element is situated near a second end of the bearing sleeve, the sensor which is rigidly mounted near said second end being operative to supply an output signal which is dependent on a lateral displacement of the control element. The control element is preferably formed by a pin which laterally projects from the bearing sleeve and which is made of a magnetically conductive material, the sensor being a magnetic sensor. Magnetic sensors are rugged and reliable.

A further preferred embodiment of the device in accordance with the invention is characterized in that there is provided a second drive mechanism which is operative to tilt the table top relative to the table support about a horizontal shaft which extends transversely of the longitudinal direction of the table top, there also being provided compensation means which are operative to exert a force on the table top which is directed upwards in the longitudinal direction of the table top and is dependent on the total mass of the table top plus a load present thereon and on the angle wherethrough the table top has been tilted relative to the horizontal position, said force being substantially equal to the force exerted downwards by gravity in the longitudinal direction of the table top. As a result of the presence of the compensation means, the person operating the apparatus experiences hardly any difference between the horizontal position and an oblique position of the table top.

BRIEF DESCRIPTION OF THE DRAWINGS

These and other aspects of the invention will be described in detail hereinafter with reference to the drawing, wherein.

DETAILED DESCRIPTION OF THE PREFERRED EMBODIMENTS

Figure 1:
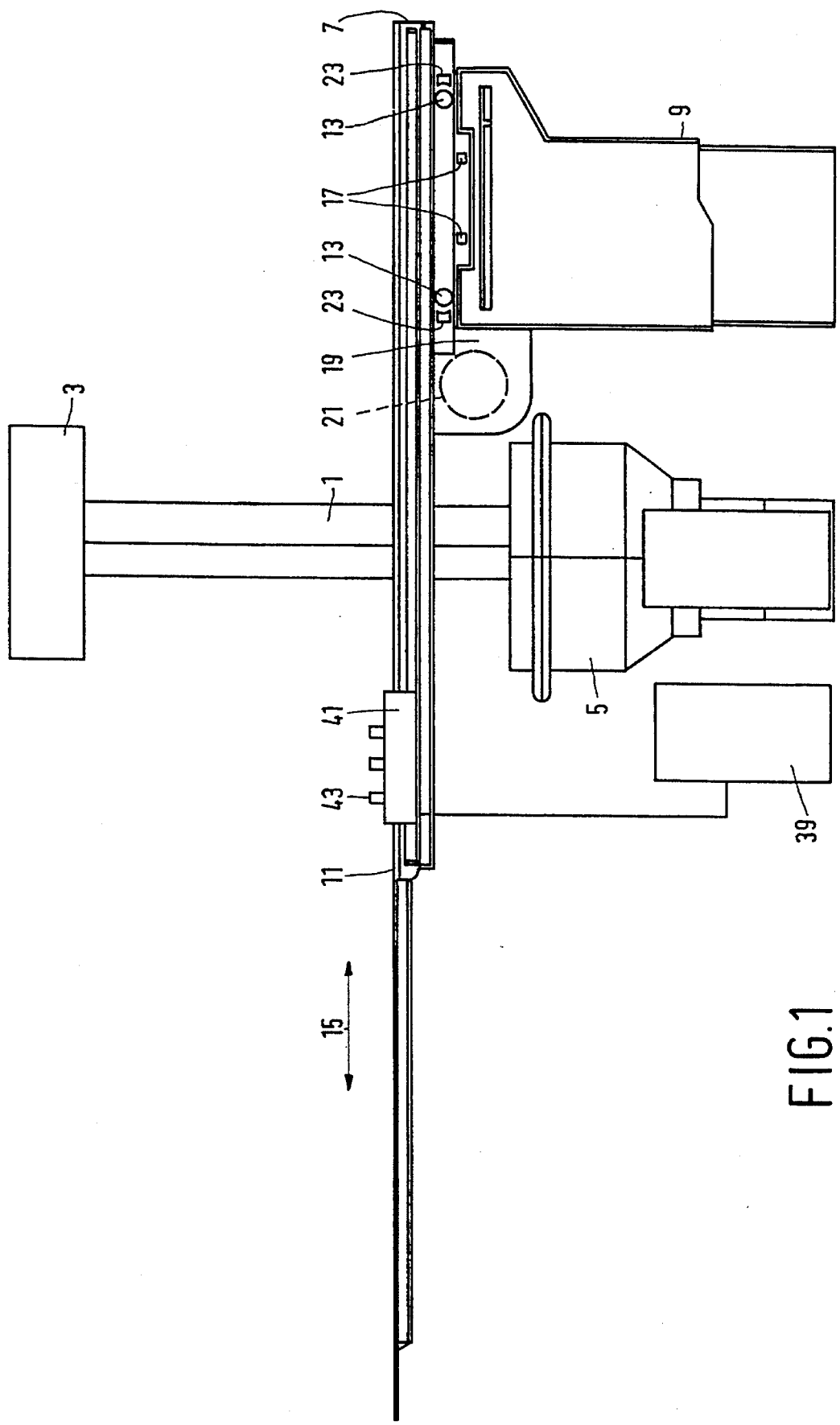
FIG. 1 is a side elevation of an embodiment of a medical apparatus in accordance with the invention.

The apparatus shown in FIG. 1 is an X-ray examination apparatus which comprises a support 1, for example a C-arm, whereto an X-ray source 3 and an X-ray detector 5, for example an X-ray image intensifier tube, are connected. The support 1 is secured to the ceiling or to the floor of an examination space so as to be movable relative to a patient table 7. The patient table 7 comprises a table support 9 and a table top 11 which is connected to the table support. Between the table top 11 and the table support 9 there are provided first rollers 13 which enable movement of the table top in the longitudinal direction (in conformity with the double arrow 15). Preferably, there are also provided second rollers 17 which enable movement of the table top parallel to its plane perpendicular to the direction denoted by the arrow 15 (i.e. perpendicularly to the plane of drawing). For the movement of the table top 11 in the direction of the arrow 15 there is provided a first drive mechanism which comprises, for example a motor 21 (denoted by a dashed line) which is accommodated in a motor housing 19. The motor 21 drives one or more of the first rollers 13 via a transmission which is not shown in FIG. 1 (for example, a chain or a drive belt). The table top 11 can be locked in any desired position by means of a locking mechanism which comprises, for example brake blocks 23 which can be pressed against the first rollers 13 by way of an electromagnetic drive (not shown). The second rollers 17 may also be provided with brake blocks (not shown). Instead of a drive belt or chain, the first drive mechanism may also comprise other known transmissions, for example a rack and pinion.

A patient to be examined can be arranged on the table top 11, the patient then being irradiated by an X-ray beam which originates from the X-ray source 3 and which is incident on the X-ray image intensifier 5 after having traversed the patient. Because the table top 11 and the support 1 are movable, different parts of the patient can be irradiated from different directions. For some examinations it is also desirable that the patient is in a position other than the horizontal position. To this end there is preferably provided a second drive mechanism which will be described in brief with reference to FIG. 2.

Figure 2:
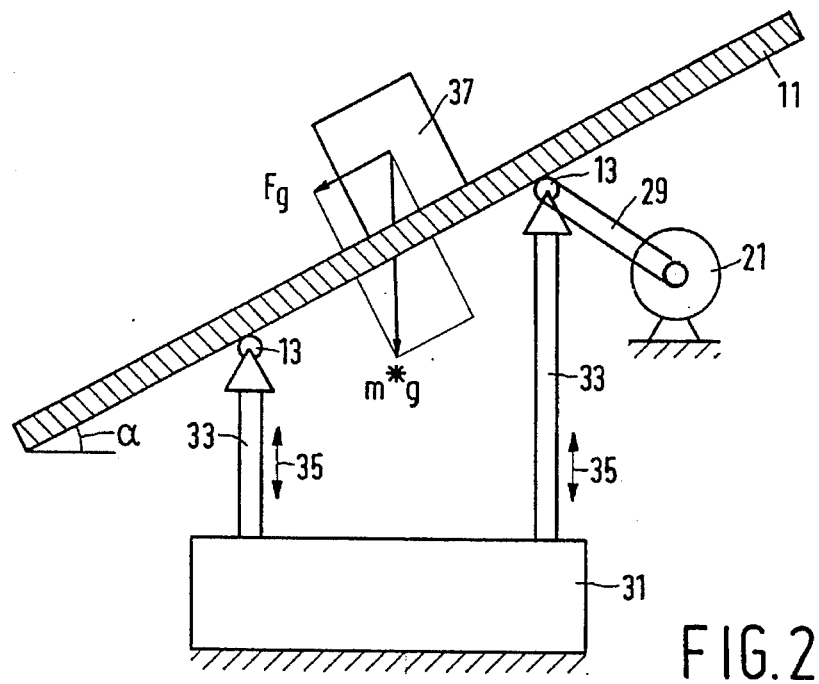
FIG. 2 is a diagrammatic representation of a part of the drive mechanisms of the apparatus shown in FIG. 1.

FIG. 2 shows diagrammatically the table top 11 with the first rollers 13 and the motor 21 which forms part of the first drive mechanism and which drives one or more of the first rollers via a chain 29. The second drive mechanism 31 is a mechanism which is known per se and which comprises a motor (not shown) which drives vertical rods 33, for example hydraulically or via toothed racks, the first rollers 13 being secured to the upper ends of said vertical rods. Consequently, the rods 33 move in the vertical direction, together with the first rollers 13, as denoted by the double arrows 35. Because the movement of the rods 33 can be separately controlled, the table top 11 can thus be tilted about a horizontal shaft which extends transversely of the longitudinal direction of the table top, so that the plane of the table top can be adjusted so as to enclose an arbitrary angle $\alpha$ relative to the horizontal plane. When a load 37 (for example, a patient) is positioned on the table top 11, gravity exerts a vertically directed force m·g on the combination formed by the table top and the load, in which m is the total mass of the table top plus the load and g is the acceleration of the force of gravity. When the table top 11 encloses an angle $\alpha$ relative to the horizontal plane, this force has a component $F_g$ which is directed downwards in the longitudinal direction of the table top. $F_g$ is then equal to m·g·sin($\alpha$). The first drive device 21 is preferably controlled so that this drive device exerts a force on the table top 11, which is directed upwards in the longitudinal direction of the table top and which is substantially equal to the force $F_g$. To this end, the patient table 7 may be provided with an angle detector for measuring the angle $\alpha$, for example as described in US-A-3 822 875 and with a weighing mechanism for determining the total mass (not shown). On the basis of this data a central control unit 39 (see FIG. 1) can calculate the drive force to be exerted on the table top 11 by the motor 21, and supply the motor with an appropriate control signal. Evidently, it is also possible to provide a separate drive mechanism for compensation of the force $F_g$, so that the first drive mechanism 21 serves exclusively for moving the table top 11 in the longitudinal direction.

For operation of the apparatus a console 41 is attached to the patient table 7 and connected to the control unit 39 which supplies inter alia control signals for the first drive mechanism 21 and the locking mechanism 23. To this end, the console 41 is provided with a number of control members, one of which is denoted by the reference numeral 43. The control member 43 serves as a common control member for the first drive mechanism 21 and the locking mechanism 23. The construction of this common control member 43 will be described in detail hereinafter with reference to FIG. 3.

Figure 3:
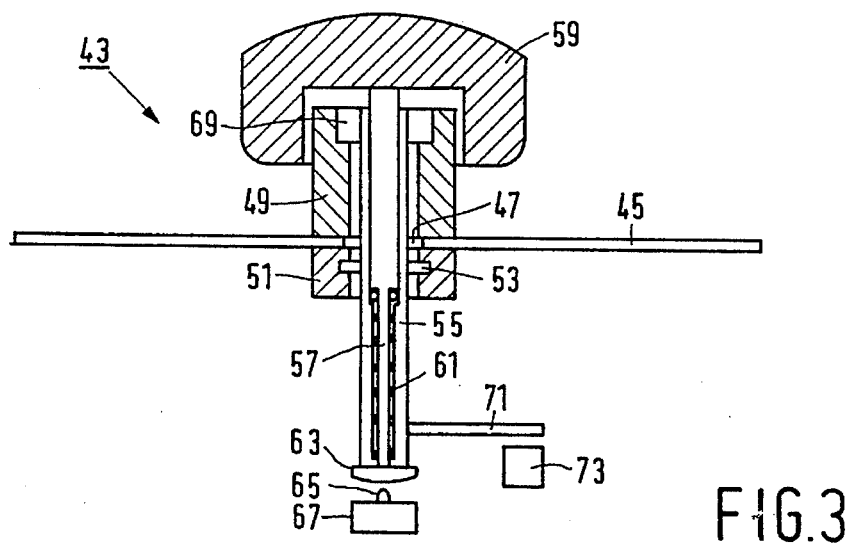
FIG. 3 is a longitudinal sectional view of an embodiment of a control member for the apparatus shown in FIG. 1, and FIGS. 4A and 4B are a plan view and a side elevation, respectively, of the link between a control element and a sensor which form part of the control member shown in FIG. 3.

FIG. 3 shows a front plate 45 of the console 41 in which there is provided an opening 47. At the area of the opening 47 a support 49 is secured to the upper side of the front plate 45; at its lower side there is provided a bearing 51 in which a horizontal shaft 53 is journalled. A bearing sleeve 55 which extends vertically through the opening 47 can be tilted about the shaft 53. A link rod 57 which also extends vertically through the opening 47 is journalled in the bearing sleeve 55 so that it is movable in its longitudinal direction. A control knob 59 is mounted on a first end of the link rod 57 (the upper end in FIG. 3). Between the link rod 57 and the bearing sleeve 55 there is provided a resilient element in the form of a helical spring 61 which exerts a force on the link rod so that the link rod is forced in a first position. The link rod 57 can be moved downwards, against the force of the spring 61, by exerting a pressure on the control knob 59, until it occupies a second position which is lower than the first position. In the embodiment shown, the second end (the lower one in FIG. 3) of the link rod 57 is provided with a disc-like control element 63 which can cooperate with a pushbutton 65 of a switch 67 which is operative to make the central control unit 39 supply a signal which switches the locking device 23 on or off. The locking device 23 can then be switched off, for example by depression of the control knob 59. Evidently, other types of switch can also be used, for example a switch which is responsive to a magnetic field in combination with a control element 63 in the form of a permanent magnet.

When a lateral force is exerted on the control knob 59 (in one of the two directions perpendicular to the plane of drawing), this force is transferred to the bearing sleeve 55 via the link rod 57, so that the sleeve is tilted about the shaft 53. If desired, the control knob 59 may also be directly connected to the bearing sleeve 55. Near a first end (the upper end in FIG. 3), situated in the vicinity of the first end of the link rod 57, the bearing sleeve 55 is mounted in a resilient ring 69 which exerts a force on the bearing sleeve which drives the bearing sleeve to a neutral position in which it extends substantially vertically. This force must be overcome in order to tilt the bearing sleeve 55. Near its second end (the lower end in FIG. 3) the bearing sleeve 55 is provided with a control element in the form of a pin 71 which laterally projects from the bearing sleeve and which cooperates with a sensor 73 which is operative to detect a displacement of the pin. The pin 71 is preferably made of a magnetically conductive material. The sensor 73 may be a magnet sensor as will be described with reference to FIG. 4. Other combinations of control elements and sensors, of course, are also feasible. For example, the control element 71 may comprise a light source and the sensor 73 may be a light-sensitive detector which produces a signal which is dependent on the location of the light source. The control element 71 may also be connected directly to the link rod 57, if desired, so that the bearing sleeve may be shorter or even be completely dispensed with. Regardless of the construction, the sensor 73 produces an output signal which is a measure of the lateral deflection of the bearing sleeve 55, and hence of the magnitude of the lateral force exerted on the control knob 59. This output signal is applied to the central control unit 39 which responds by applying an appropriate control signal to the first drive mechanism 21.

Figure 4A:
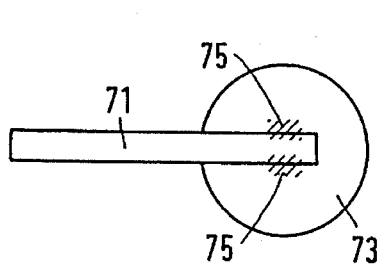
Figure 4B:
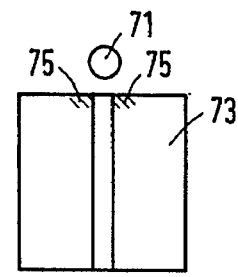

FIGS. 4A and 4B show some details of the above preferred embodiment of the combination formed by the control element 71 and the sensor 73. In the present embodiment, the control element 71 is formed by a pin of a magnetically conductive material, for example iron. The sensor 73 is a magnetic sensor, i.e. a sensor which detects disturbances of a magnetic field in its vicinity. Such disturbances are dependent on the position of the pin 71. The sensor comprises an approximately cylindrical housing, on one of the end faces of which there are provided magnetoresistive resistors 75. The housing accommodates a permanent magnet and an electronic circuit (not shown). When the pin 71 occupies a symmetrical position relative to the magnetoresistive resistors, as shown in FIG. 4, the sensor 73 produces an output voltage which equals zero. When the position of the pin 71 deviates from this neutral position in the one or the other direction, the sensor 73 produces a positive or a negative output voltage, respectively. A suitable sensor is, for example the Siemens sensor type number The table top 11 can be moved in the direction of the arrow 15 by means of the common control member 43. This can be realized by exerting a force by hand, via the control knob 59, on the table top 11 or by making the drive mechanism 21, controlled via the common control member 43, assist the movement. This drive mechanism is then controlled by signals which are supplied by the central control unit 39 in response to the output signal of the sensor 73. If the table top is not in the horizontal position, the central control unit 39 also ensures that the downwards directed force $F_g$ in the longitudinal direction of the table top is compensated for as described with reference to FIG. 2. The table top 11 can also be displaced perpendicularly to the plane of drawing of FIG. 1 by means of the common control member 43. Generally speaking, no assistance from a drive mechanism is required for the latter displacement. Finally, the table top 11 can be locked in any desired position by the common control member by releasing the control knob 59. Via the common control member 43, the movements of the table top can thus be controlled with one hand.

I claim:

1. A medical apparatus, comprising a patient table with a table support and a table top which is movable at least in a longitudinal direction of the table top relative to the table support, a first motorized drive mechanism which selectively assists this movement, a locking mechanism for selectively locking said table top relative to the table support, and a common control member controlling both the first drive mechanism and the locking mechanism, said control member comprising a link rod which is movable in a longitudinal direction of the link rod and which cooperates with a switch in order to control the locking mechanism, and also comprises a control element which is movable transversely of the longitudinal direction of the link rod and which cooperates with a sensor which supplies an output signal for operating the drive mechanism which is a measure of the amount of displacement of the control element transversely of the longitudinal direction of the link rod, the link rod and the control element being movable by means of a common control knob whereby the table top can be moved also without assistance from the first drive mechanism.

2. An apparatus as claimed in claim 1, wherein the link rod is journalled so as to be movable in its longitudinal direction in a bearing sleeve, which supports the control element and which can be tilted about a shaft extending transversely of its longitudinal direction, the control knob being attached to a first end of the link rod which is situated near a first end of the bearing sleeve, the arrangement being such that by pressing the control knob, the link rod can be moved in its longitudinal direction from a first position to a second position, the bearing sleeve itself being tiltable about said shaft from a neutral position into two opposite directions, under the influence of a lateral force exerted on the control knob, the force exerted on the control knob being transferred to the bearing sleeve via the link rod.

3. An apparatus as claimed in claim 2, further comprising first resilient means which exert a force on the link rod which drives the link rod to its first position, and second resilient means which exert a force on the bearing sleeve which drives the bearing sleeve to its neutral position.

4. An apparatus as claimed in claim 2, wherein near a second end the link rod is provided with a control element for operating the switch.

5. An apparatus as claimed in claim 4, wherein the control element is situated near a second end of the bearing sleeve, and the sensor is rigidly mounted near said second end.

6. An apparatus as claimed in claim 5, wherein the control element is formed by a pin which laterally projects from the bearing sleeve and which is made of a magnetically conductive material, the sensor being a magnetic sensor.

7. An apparatus as claimed in claim 3, wherein the control element is situated near a second end of the bearing sleeve, and the sensor is rigidly mounted near said second end.

8. An apparatus as claimed in claim 7, wherein the control element is formed by a pin which laterally projects from the bearing sleeve and which is made of a magnetically conductive material, the sensor being a magnetic sensor.

9. An apparatus as claimed in claim 2, wherein the control element is situated near a second end of the bearing sleeve, and the sensor is rigidly mounted near said second end.

10. An apparatus as claimed in claim 2, wherein near a second end the link rod is provided with a control element for operating the switch.

11. An apparatus as claimed in claim 10, wherein the control element is situated near a second end of the bearing sleeve, and the sensor is rigidly mounted near said second end.

12. An apparatus as claimed in claim 11, wherein the control element is formed by a pin which laterally projects from the bearing sleeve and which is made of a magnetically conductive material, the sensor being a magnetic sensor.

13. An apparatus as claimed in claim 2, wherein there is provided a second drive mechanism which is operative to tilt the table top relative to the table support about a horizontal shaft which extends transversely of the longitudinal direction of the table top, there also being provided compensation means which are operative to exert a force on the table top which is directed upwards in the longitudinal direction of the table top and is dependent on the total mass of the table top plus a load present thereon and on an angle wherethrough the table top has been tilted relative to the horizontal position, said force being substantially equal to the force exerted downwards by gravity in the longitudinal direction of the table top.

14. An apparatus as claimed in claim 1, wherein near a second end the link rod is provided with a control element for operating the switch.

15. An apparatus as claimed in claim 14, wherein the control element is situated near a second end of the bearing sleeve, and the sensor is rigidly mounted near said second end.

16. An apparatus as claimed in claim 15, wherein the control element is formed by a pin which laterally projects from the bearing sleeve and which is made of a magnetically conductive material, the sensor being a magnetic sensor.

17. An apparatus as claimed in claim 1, wherein there is provided a second drive mechanism which is operative to tilt the table top relative to the table support about a horizontal shaft which extends transversely of the longitudinal direction of the table top, there also being provided compensation means which are operative to exert a force on the table top which is directed upwards in the longitudinal direction of the table top and is dependent on the total mass of the table top plus a load present thereon and on an angle wherethrough the table top has been tilted relative to the horizontal position, said force being substantially equal to the force exerted downwards by gravity in the longitudinal direction of the table top.

18. An apparatus as claimed in claim 17, wherein the first drive mechanism forms part of the compensation means.

19. A medical apparatus, comprising a patient table with a table support and a table top which is movable at least in a longitudinal direction of the table top relative to the table support, there being provided a first drive mechanism for selectively assisting this movement, a locking mechanism for selectively locking said table top relative to the table support, and a common control member for controlling the first drive mechanism and the locking mechanism, said control member comprising a link rod which is movable in a longitudinal direction of the link rod and which cooperates with a switch in order to control the locking mechanism, and also comprises a control element which is movable transversely of the longitudinal direction of the link rod and which cooperates with a sensor which supplies an output signal for operating the drive mechanism, the link rod and the control element being movable by means of a common control knob whereby the table top can be moved also without assistance from the first drive mechanism, wherein the link rod is journalled so as to be movable in its longitudinal direction in a bearing sleeve, which supports the control element and which can be tilted about a shaft extending transversely of its longitudinal direction, the control knob being attached to a first end of the link rod which is situated near a first end of the bearing sleeve, the arrangement being such that by pressing the control knob, the link rod can be moved in its longitudinal direction from a first position to a second position, the bearing sleeve itself being tiltable about said shaft from a neutral position into two opposite directions, under the influence of a lateral force exerted on the control knob, the force exerted on the control knob being transferred to the bearing sleeve via the link rod, wherein the control element is situated near a second end of the bearing sleeve, and the sensor is rigidly mounted near said second end and is operative to supply an output signal which is dependent on a lateral displacement of the control element, and wherein the control element is formed by a pin which laterally projects from the bearing sleeve and which is made of a magnetically conductive material, the sensor being a magnetic sensor.

* * * * *